United States Patent
Blaeser et al.

(10) Patent No.: US 6,168,617 B1
(45) Date of Patent: Jan. 2, 2001

(54) STENT DELIVERY SYSTEM

(75) Inventors: David J. Blaeser, Champlin; Richard C. Mattison, Zimmerman, both of MN (US)

(73) Assignee: SciMed Life Systems, Inc., Maple Grove, MN (US)

(*) Notice: Under 35 U.S.C. 154(b), the term of this patent shall be extended for 0 days.

(21) Appl. No.: 09/332,914

(22) Filed: Jun. 14, 1999

(51) Int. Cl.$^7$ ........................................ A61F 2/06
(52) U.S. Cl. ................................................ 623/1.11
(58) Field of Search ................... 606/108, 198, 606/194; 623/1.11

(56) References Cited

U.S. PATENT DOCUMENTS

| | | |
|---|---|---|
| 4,733,665 | 3/1988 | Palmaz . |
| 4,740,207 | 4/1988 | Kreamer . |
| 4,950,227 | 8/1990 | Savin et al. . |
| 5,007,926 | 4/1991 | Derbyshire . |
| 5,026,377 | 6/1991 | Burton et al. . |
| 5,108,416 | 4/1992 | Ryan et al. . |
| 5,158,548 | 10/1992 | Lau et al. . |
| 5,201,757 | 4/1993 | Heyn et al. . |
| 5,242,399 | 9/1993 | Lau et al. . |
| 5,290,295 | 3/1994 | Querals et al. . |
| 5,342,307 | 8/1994 | Euteneuer et al. . |
| 5,344,426 | 9/1994 | Lau et al. . |
| 5,360,401 | 11/1994 | Turnland . |
| 5,403,341 | 4/1995 | Solar . |
| 5,415,664 | 5/1995 | Pinchuk . |
| 5,445,646 | 8/1995 | Euteneuer et al. . |
| 5,453,090 | 9/1995 | Martinez et al. . |
| 5,458,605 | 10/1995 | Klemm . |
| 5,458,615 | 10/1995 | Klemm et al. . |
| 5,517,135 | 5/1996 | Young . |
| 5,534,007 | 7/1996 | St. Germain et al. . |
| 5,545,209 | 8/1996 | Roberts et al. . |
| 5,571,135 | 11/1996 | Fraser et al. . |
| 5,571,168 | * 11/1996 | Toro . |
| 5,634,928 | * 6/1997 | Fischell et al. . |
| 5,662,703 | * 9/1997 | Yurek et al. . |
| 5,693,034 | 12/1997 | Buscemi et al. . |
| 5,733,267 | * 3/1998 | Del Toro . |
| 5,735,859 | * 4/1998 | Fischell et al. ................. 606/108 |
| 5,772,669 | * 6/1998 | Vrba ................................ 606/108 |

(List continued on next page.)

FOREIGN PATENT DOCUMENTS

| | | |
|---|---|---|
| 0 707 837 A1 | 4/1996 | (EP) . |
| WO 96/03092 A1 | 2/1996 | (WO) . |
| WO 98/07388 | 2/1998 | (WO) . |
| WO 98/07390 | 2/1998 | (WO) . |
| WO 98/09583 | 3/1998 | (WO) . |

* cited by examiner

Primary Examiner—Gene Mancene
Assistant Examiner—Eduardo C. Robert
(74) Attorney, Agent, or Firm—Vidas, Arrett & Steinkraus

(57) ABSTRACT

The present invention provides an apparatus for delivery and deployment of an expandable stent within a vessel. The apparatus comprises a catheter having a proximal end, a distal end and a catheter shaft, an expandable stent coaxially mounted on the catheter near the distal end of the catheter and a securement apparatus coaxially mounted on the catheter near its distal end and over the stent. The securement apparatus comprises a securement sleeve having a proximal end, a distal end, an exterior surface and an interior surface. The securement sleeve is constructed and arranged for proximal advancement along the catheter shaft. The present invention also includes a distal cuff having a proximal end, a distal end, an exterior surface and an interior surface. The distal cuff is mounted near the distal end of the catheter and is constructed and arranged to closely surround the exterior surface of the securement sleeve at the distal end of the securement sleeve until proximal advancement thereof and subsequent deployment of the stent.

10 Claims, 4 Drawing Sheets

U.S. PATENT DOCUMENTS

| | | | |
|---|---|---|---|
| 5,782,855 | * 7/1998 | Lau et al. | 606/108 |
| 5,800,517 | * 9/1998 | Anderson et al. | |
| 5,830,217 | * 11/1998 | Ryan | 606/108 |
| 5,843,090 | * 12/1998 | Schuetz | 606/108 |
| 5,843,092 | * 12/1998 | Heller et al. | 606/108 |
| 5,908,448 | * 6/1999 | Roberts et al. | 606/194 |
| 5,944,726 | * 8/1999 | Blaeser et al. | 606/108 |

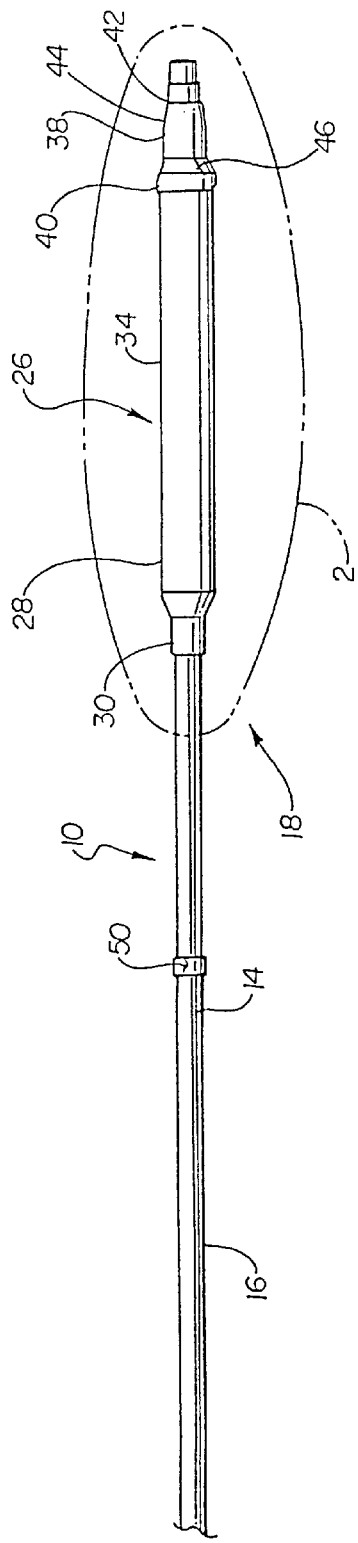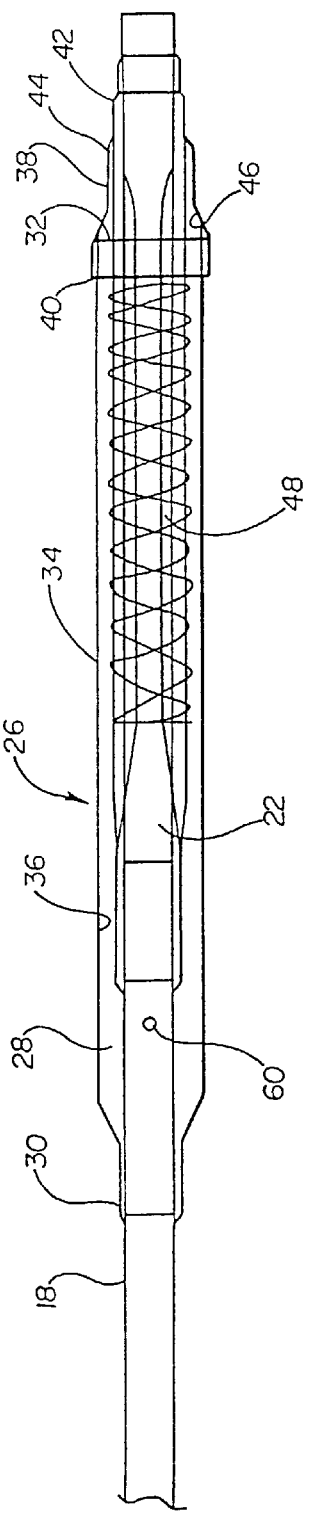

STENT DELIVERY SYSTEM

FIELD OF THE INVENTION

This invention relates to an assembly and method for delivering and deploying an expandable stent, particularly within a lumen of a body vessel. More specifically, this invention relates an assembly and method for delivering and deploying a balloon expandable stent, and most notably to stent securement devices positioned over the balloon and stent.

BACKGROUND OF THE INVENTION

Stents and stent delivery assemblies are utilized in a number of medical procedures and situations, and as such their structure and function are well-known. A stent is a general cylindrical prosthesis introduced via a catheter into a lumen of a body vessel, the stent being in a configuration having a generally reduced diameter and then being expanded to the diameter of the vessel. In its expanded configuration, the stent supports and reinforces the vessel walls while maintaining the vessel in an open, unobstructed condition.

Both self-expanding and inflation (as by a balloon) expandable stents are well-known and widely available. Self-expanding stents must be maintained under positive external pressure in order to maintain their reduced diameter configuration during delivery of the stent to its deployment site. Inflation expandable stents (also known as balloon expandable stents) are generally crimped to their reduced diameter about the delivery catheter, positioned at the deployment site, and then expanded to the vessel diameter by fluid inflation of the balloon positioned between the stent and the delivery catheter. The present invention is particularly concerned with stent securement in the delivery and deployment of inflation expandable stents.

In angioplasty procedure, there may be restenosis of the artery, which either necessitates another angioplasty procedure, a surgical bypass procedure, or some method of repairing or strengthening the area. To prevent restenosis and strengthen the area, a physician may implant an intravascular prosthesis for maintaining vascular patency, i.e. a stent, inside the artery at the lesion. The stent is expanded to a larger diameter following placement in the vasculature, often by a balloon portion of the catheter. Stents delivered to a restricted coronary artery, expanded to a larger diameter as by a balloon catheter, and left in place in the artery at the site of a dilated lesion are shown in U.S. Pat. No. 4,740,207 to Kreamer; U.S. Pat. No. 5,007,926 to Derbyshire; U.S. Pat. No. 4,733,665 to Palmaz; U.S. Pat. No. 5,026,377 to Burton et al.; U.S. Pat. No. 5,158,548 to Lau et al.; U.S. Pat. No. 5,242,399 to Lau et al.; U.S. Pat. No. 5,344,426 to Lau et al.; U.S. Pat. No. 5,415,664 to Pinchuck; U.S. Pat. No. 5,453,090 to Martinez et al.; U.S. Pat. No. 4,950,227 to Savin; U.S. Pat. No. 5,403,341 to Solar; U.S. Pat. No. 5,108,416 to Ryan et al.; and European Patent Application No. 707837A1 to Scheiban, all of which are incorporated herein by reference. A stent particularly preferred for use with this invention is described in PCT Application No. 96/03092-A1, published Feb. 8, 1996, the content of which is also incorporated herein by reference.

In advancing a inflation expandable stent through a body vessel to the deployment site, there are a number of important considerations. The stent must be able to securely maintain its axial position on the delivery catheter. The stent, particularly its distal and proximal ends, are sometimes protected to prevent distortion of the stent, and minimize trauma to the vessel walls. Balloon expandable stent delivery and deployment assemblies are known which utilize restraining means that overlie the stent during delivery. U.S. Pat. No. 4,950,227 to Savin et al., relates to a balloon expandable stent delivery system in which a sleeve overlaps the distal or proximal margin (or both) of a stent during delivery. During inflation of the stent at the deployment site, the stent margins are freed of the protective sleeve(s) and the sleeve(s) then collapse upon the delivery catheter for removal. U.S. Pat. No. 5,403,341 to Solar, relates to stent delivery and deployment assembly which uses retaining sheaths positioned about opposite ends of the compressed stent. The retaining sheaths of Solar are adapted to tear under pressure as the stent is radially expanded, thus releasing the stent for engagement with the implant site. U.S. Pat. No. 5,108,416 to Ryan et al. describes a stent introducer system which uses one or two flexible end caps and an annular socket surrounding the balloon to position the stent during introduction to the deployment site. The content of all of these patents is incorporated herein by reference.

In positioning a balloon expandable stent on a delivery catheter over a fluid expandable balloon, the stent is preferably smoothly and evenly crimped to closely conform to the overall profile of the catheter and the unexpanded balloon. It has been noted that, due to physical properties of the material used in manufacturing stents (typically stainless steel or a shape memory metal, such as Nitinol™) there is a certain amount of "recoil" of the stent despite the most careful and firm crimping. That is the stent evidences a tendency to slightly open up from the fully crimped position once the crimping force has been released. For example, in a typical stainless steel stent delivery and deployment assembly, if the stent has been fully crimped to a diameter of approximately 0.0035", such stents have been observed to open up or recoil to approximately 0.0037" in diameter. This phenomenon has been characterized as "recoil crimping". Due to recoil crimping to this slightly enlarged diameter, it can be understood that stents in such instances may tend to evidence a certain amount of looseness from their desired close adherence to the overall profile of the underlying catheter and balloon. That is, such stents may tend to have a perceptible relatively slack fit in their mounted and crimped position. During delivery, such a stent may thus tend to slip or dislocate from a desired position on the catheter or even become separated from the catheter, requiring further intervention by the physician.

One important characteristic of a balloon catheter is its "profile", which is determined by the outer diameter (O.D.) of the distal end portion of the catheter, which includes a balloon and stent when the combination is in its delivery profile. The outer diameter affects the ease and ability of the catheter to pass through a guide catheter, through coronary arteries for example, and across a tight lesion site. Considerable effort has been made in developing low profile balloon catheters. U.S. Pat. No. 5,342,307, incorporated herein by reference, discloses a balloon protector sleeve used with a tri-fold balloon catheter for angioplasty. Minimization of "profile" is of importance in balloon catheters and stent delivery systems.

SUMMARY OF THE INVENTION

The present invention is particularly directed to improved arrangements to secure and cover a stent on a delivery catheter to better facilitate delivery thereof. The securement devices secure the stent to the catheter during tracking and delivery. The present invention also provides an improved arrangement of a stent delivery system with a minimized profile.

The stent securement device of the present invention is of particular utility with such stent delivery systems as are set forth in U.S. Pat. No. 5,571,168 and 5,733,267 for PULL BACK STENT DELIVERY SYSTEM, U.S. Application Ser. No. 09/052,488 filed Mar. 31, 1998, U.S. Application Ser. No. 08/807,791 filed Feb. 28, 1997, U.S. Application Ser. No. 08/702,150 filed Aug. 23, 1996, U.S. Application Ser. No. 08/697,453 filed Aug. 23, 1996, U.S. Application Ser. No. 08/101,979, filed Aug. 23, 1997, U.S. Application Ser. No. 08/702,149 filed Aug. 23, 1996, International Application PCT/US97/14980, and International Application PCT/US97/14141, all of which are incorporated by reference in their entirety.

BRIEF DESCRIPTION OF THE FIGURES

FIG. 1 is a side view of the distal end of a stent delivery system including a stent securement means according to the present invention;

FIG. 2 is an enlarged longitudinal view in schematic of the distal portion of the catheter of FIG. 1 (indicated by dashed circle 2 in FIG. 1);

DESCRIPTION OF THE PREFERRED EMBODIMENTS

Figure 3:
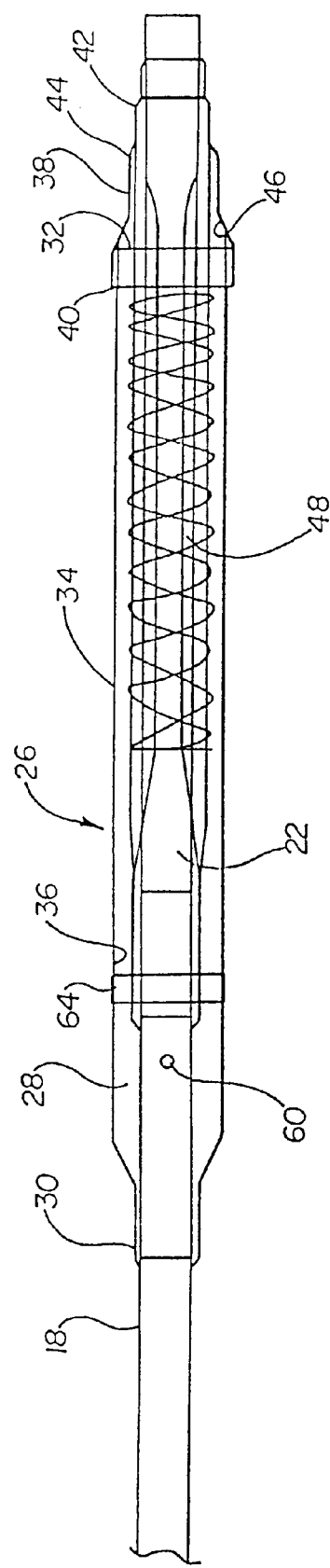
FIG. 3 is longitudinal view of the distal portion of the catheter similar to FIG. 2 with an alternative proximal advancement means for the sheath of the stent securement means.

Referring to FIGS. 1–3, a medical device comprising a stent delivery catheter system comprising a stent delivery catheter with a stent securement means according to the present invention is generally indicated at 10.

As shown at FIG. 1, catheter 10 has a shaft 14, a proximal portion 16 and a distal portion 18. Distal portion 18 is fixed to shaft 14 by standard means known in the art. For instance, distal portion 18 may be bonded at its ends by adhesive to the catheter in an integral manner, or may be made one-piece with the catheter as is known in the art.

Referring to FIGS. 2–3, distal portion 18 (dashed circle of FIG. 1) is shown in enlarged longitudinal cross-sectional view. Distal end portion 18 comprises balloon 22, which is constructed and arranged for expansion from a contracted state to an expanded state.

Balloon 22 may be of any length. For instance, balloon 22 may be about 15 mm long. This length, however, is for illustrative purposes only and is not meant to be limiting. Balloon 22 is shown in a folded, contracted state in FIGS. 2–3. Balloon 22 may be, and preferably is, made of a material which resiliently deforms under radial pressure. Examples of suitable materials are generally known in the art and include non-compliant, semi-compliant and compliant materials such as polyethylene (PE), nylon, polyether block amides (PEBAX), polyethylene terephthalate (PET), silicone, POC, a polyethylene, a polyether, or polyesters such as Hytrel™.

In use, balloon 22 has a larger diameter which is obtained when the balloon 22 is expanded in the known manner. Catheter balloon 22 may be inflated by fluid (gas or liquid) from an inflation port (not shown) extending from an inflation lumen contained in the catheter shaft 14 and opening into the balloon 22, or by other means, such as from fluid communication from a passageway or passageways formed between the outside of the catheter shaft and the membrane forming the balloon, depending on the design of the catheter, all of which are known in the art. The passageway(s) may extend from the catheter shaft directly to the interior of the balloon or may extend to the exterior of the balloon. The catheter may alternatively be associated with a source of fluid (gas or liquid) external to the catheter (not shown), whereby the fluid is delivered to the balloon or expandable member by an inflation lumen located in the catheter shaft 14 and associated with the balloon 22 as is known in the art. The details and mechanics of balloon inflation and specific overall catheter construction will vary according to the design of the catheter, and are known in the art per se. All of these variations are acceptable for use with the balloon catheters and stent delivery systems of the present invention.

Stent delivery system 10 further comprises stent securement means, such as a sheath, indicated generally at 26 in FIGS. 1–3, comprising a very flexible thin walled sleeve or sheath 28 having a proximal end 30, a distal end 32 (as shown specifically in FIGS. 2–6), an exterior surface 34 and an interior surface 36, and a distal elastomeric sock, cuff or collar 38 (shown in FIGS. 1–3), having a proximal end 40, a distal end 42, exterior surface 44 and an interior surface 46. Preferred materials for sheath 28 are PTFE and HDPE, although other materials may be used. Preferred wall thickness is 0.005 inches although this dimension is not critical. Preferably the material is as thin as possible consistent with the constitutional strength of the sheath. The distal end of the sheath 28 is tucked under sock 38. Preferred materials for sock 38 are urethane elastomers.

Stent securement means 26 serves to secure and cover stent 48 during delivery thereof. Any suitable balloon expandable stent or equivalent known in the art may be delivered by the stent delivery system of the present invention.

Stent 48, in its delivery diameter, and balloon 22 are coaxially mounted at the distal end 18 of catheter 10 such that stent 48 is mounted axially over balloon 22 as shown in FIGS. 2 and 3. In the preferred embodiment, expandable balloon 22 is designed and adapted for expansion of the stent from the delivery diameter to the deployment diameter upon application of fluid deployment pressure to the balloon as is known in the art.

The most unique features of stent securement means 26 of the present invention are the thin, very flexible stent sheath 28, its distal elastomeric cuff 38 and the tuck under relationship thereof. The advantages provided by these features are the superior stent securement provided thereby, the minimization of trauma to the vessel walls provided by sheath 28, the securement of the stent during tracking and delivery which prevents distortion of stent 48, the maintenance of the balloon and stent position in an artery during stent deployment, and the ready release of the sheath and release of the balloon provided by this combination. Sheath 28 may be slip coated to further improve trackability.

A focus of the invention is the protective sheath 28 distally captured by sock 38. Although socks for capturing stents are known in the art as indicated hereinabove, an ultrathin sheath which covers the stent and is distally captured by a sock is new in the art. Distal cuff or sock 38 may have some elastic characteristics or just a gripping ability to provide a modest interference fit. A PTFE sheath— moderately heat shrunk so that there is some gripping of sheath 28 will most preferably meet these requirements. The thinness of sheath 28 is an important feature of the present invention. It is thin and is only present to protect the stent from catching on the body both during implantation or upon withdrawal if stent is not used. It reduces the required traversing force both to the lesion and across the lesion. Thus, its trackability improvement. The distal cuff or sock 38 is also an important feature of the invention. If the sock were not included, the sheath 28 might "umbrella", i.e., roll back during delivery of the stent or be dislodged or "ice cream" scoop, i.e., the cone might be moved to one side. In light of these features, stent securement means 26 of the present invention is of particular utility with delivery systems for balloon expandable stents. In addition, stent securement means 26 may be used with a delivery system for an expandable stent further comprising a storage sleeve as set forth in U.S. Pat. No. 5,800,517 issued Sep. 1, 1998 and incorporated herein by reference. Generally a stent delivery system with the stent securement means of the present invention is not provided with an additional balloon or stent protector.

Sheath 28 is axially movable on shaft 14 of catheter 10 so that it can be remotely retracted from over stent 48 as is known in the art. Stent securement means 26 is associated with a pull back means (not shown) for proximal retraction of sheath 28. In a preferred embodiment, stent securement means 26 of the present invention is associated with a wire pull back system for proximal retraction of sheath 28 in order to expose the stent for expansion. The pull back wire (not shown) is constructed and arranged to operate through port 60, best seen in FIG. 2, to proximally retract sheath 28. Proximal retraction of sheath 28 is limited by stop collar 50 (seen in FIG. 1). Such arrangements are well known in the art and need not be described here in detail to further understanding of the invention. U.S. Pat. No. 5,517,135 to Fraser et al. and U.S. Pat. No. 5,800,517 to Anderson et al., incorporated herein by reference in their entirety, are examples of such arrangements.

A full length sheath pull back system may also be used with the present invention. Stent securement device 26 of the present invention is of utility with such stent delivery systems as are set forth in U.S. Pat. Nos. 5,571,168 and 5,733,267 for PULL BACK STENT DELIVERY SYSTEM, U.S. Pat. No. 5,772,669 for STENT DEPLOYMENT CATHETER WITH RETRACTABLE SHEATH, and U.S. Pat. No. 5,534,007 for STENT DEPLOYMENT CATHETER WITH COLLAPSIBLE SHEATH all of which are incorporated herein by reference in their entirety.

Retraction or proximal advancement of sheath 28 may also be accomplished by hydraulic actuation. Referring to FIG. 3, in such a configuration wire pull back attachment means 60 would be absent and port 60 would function as a hydraulic perfusion port. Hydraulic pull-back systems are disclosed and described in U.S. Pat. Nos. 5,571,135 and 5,445,646 and in pending U.S. patent application Ser. No. 09/196,793, filed Nov. 20, 1998 entitled STENT DELIVERY DEVICE. All of these are incorporated by reference herein in their entirety.

Exterior surface 34 of sheath 28 may be coated with a silicone coating or a hydrophilic coating as a slip coating. A hydrophilic coating is preferred, such as is set forth in U.S. Pat. No. 5,693,034 directed to a Lubricious Polymer Network (incorporated herein by reference). The coating is of utility in that it assists in pulling back the system if a lesion or blockage is encountered that the system is not capable of traversing, in which case the system is pulled back into the guide catheter. Depending on the application, interior surface 36 of sheath 28 may also be coated with a silicone or hydrophilic coating. In addition, or alternatively, a silicone coating or the like may be provided at the interior surface 46 of the proximal end 40 of distal cuff 38, and the exterior surface 34 of the distal end 32 of sheath 28, to provide a slip coating between the proximal interior of distal cuff 38 and the distal exterior of sheath 28.

Figure 4:
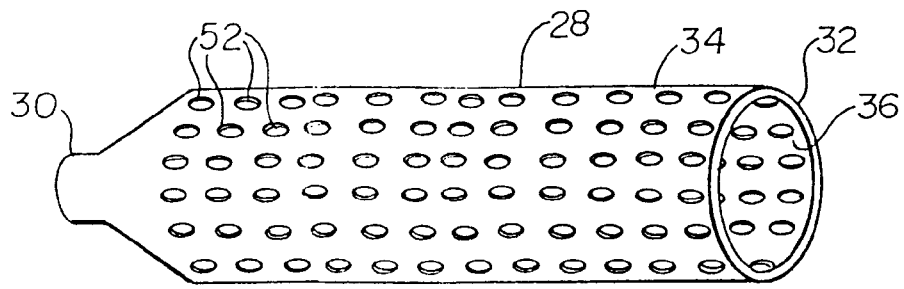
FIGS. 4–6 are perspective views of alternate embodiments of stent securement sheaths for a stent delivery system according to the present invention.
Figure 5:
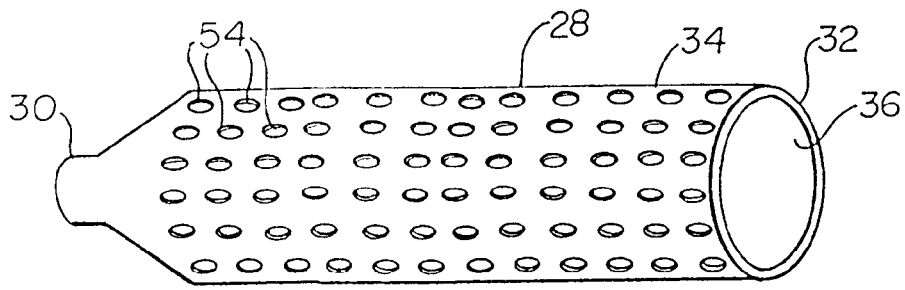
Figure 6:
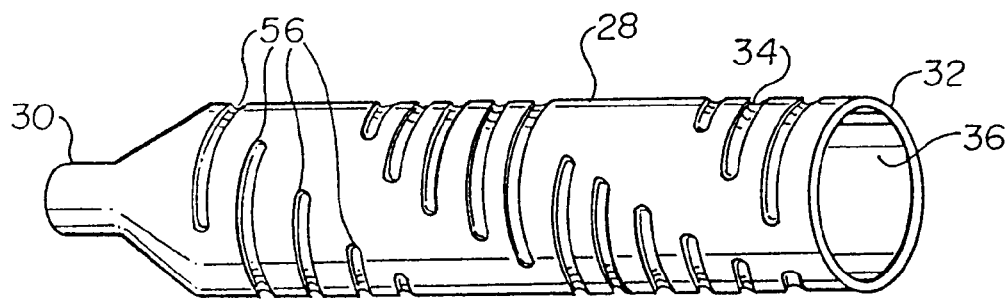

Referring to FIG. 4, sheath 28 may be provided with holes 52 to enhance flexibility. Referring to FIG. 5, if the sheath has sufficient thickness, dimples 54 may be provided, or as shown in FIG. 6, radial indentations 56 in a staggered pattern or other desired pattern may be provided.

Figure 7:
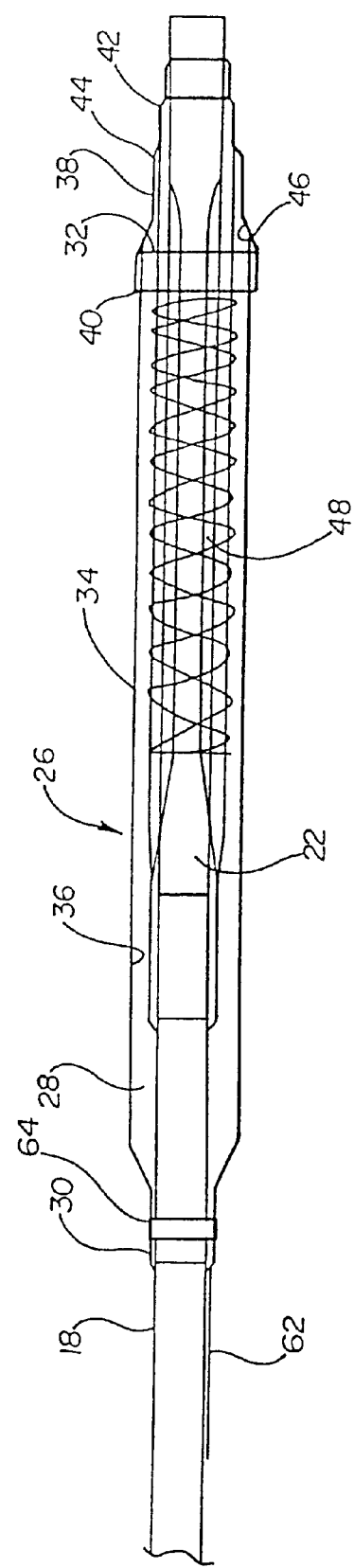
FIG. 7 is an enlarged longitudinal view in schematic of the distal portion of a catheter similar to that of FIG. 2 and showing a wire pull back means with wire.

FIG. 7 is a side profile section showing a balloon expandable stent delivery and deployment assembly, with the stent crimped to delivery diameter onto the balloon, the underlying tube component and the catheter, and also having a pull-back wire 62 attached to the sheath of the stent securement means by means of a band or collar 64.

As shown in FIG. 7, sheath 28 is slidable axially along the shaft 14 and is connected to a retracting wire 62 such that sheath 28 may be proximally advanced. The other elements of the Figure are similar to those of FIG. 2.

This description is intended to be illustrative and not exhaustive. It will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An apparatus for delivery and deployment of an expandable stent within a vessel, the apparatus comprising:
    a) a catheter having a proximal end, a middle portion, a distal end and a catheter shaft;
    b) an expandable means coaxially mounted on the catheter;
    c) an expandable stent, expandable from a delivery diameter to a deployment diameter, the stent being coaxially mounted on the catheter over the expandable means such that the expandable means is operably located axially within the stent for expansion thereof;
    d) securement means coaxially mounted on the catheter near its distal end, distal the middle portion, and over the expandable means and the stent, said securement means comprising:
        I) a securement sheath having a proximal end, a distal end, an exterior surface and an interior surface, said securement sheath being slidably mounted on the catheter shaft and being constructed and arranged for proximal retraction along the catheter shaft to expose the stent, the securement sheath having a plurality of flexibility enhancing elements; and
        ii) a distal cuff having a proximal end, a distal end, an exterior surface and an interior surface, said distal cuff being mounted near the distal end of the stent and being constructed and arranged to closely surround the exterior surface of the securement sheath at the distal end of the securement sheath until retraction thereof.

2. The apparatus of claim 1 wherein the flexibility enhancing elements comprise a plurality of holes in the securement sheath.

3. The apparatus of claim 1 wherein the flexibility enhancing elements comprise a plurality of dimples in the securement sheath.

4. The apparatus of claim 1 wherein the flexibility enhancing elements comprise a plurality of radial indentations in the securement sheath.

5. An apparatus for delivery and deployment of an expandable stent within a vessel, the apparatus comprising:
   a) a catheter having a proximal end, a distal end and a catheter shaft;
   b) an expandable means coaxially mounted on the catheter;
   c) an expandable stent, expandable from a delivery diameter to a deployment diameter, the stent being coaxially mounted on the catheter over the expandable means such that the expandable means is operably located axially within the stent for expansion thereof;
   d) securement means coaxially mounted on the catheter near its distal end, remote from the proximal end of the catheter, and over the expandable means and the stent, said securement means comprising;
      i) a securement sheath slidably sealed on the distal end of the catheter, the securement sheath having a proximal end, a distal end, an exterior surface and an interior surface, said securement sheath being constructed and arranged for proximal retraction along the catheter shaft to expose the stent, wherein the proximal end of the sheath is sealingly attached to the catheter shaft; and
      ii) a distal cuff having a proximal end, a distal end, an exterior surface and an interior surface, said distal cuff being mounted near the distal end of the stent and being constructed and arranged to closely surround the exterior surface of the securement sheath at the distal end of the securement sheath until retraction thereof;
   e) an hydraulic perfusion port in the catheter shaft located distally of the proximal end of the securement sheath, the securement sheath being constructed and arranged for retraction in response to fluid pressure; and
   f) a seal mounted on the catheter shaft, within the sheath and proximal along the catheter shaft to the stent, creating a chamber within the sheath between the seal and the slidable seal created by the proximal end of the sheath and the catheter shaft, whereby fluid or gas may be forced through the perfusion port into the chamber forcing the sheath to slide proximally to release the stent.

6. An apparatus for delivery and deployment of an expandable stent within a vessel, the apparatus comprising:
   a) a catheter having a proximal end, a middle portion, a distal end and a catheter shaft;
   b) an expandable stent, expandable from a delivery diameter to a deployment diameter, the stent being coaxially mounted on the distal end of the catheter for expansion thereof;
   d) securement means coaxially mounted on the catheter near its distal end, distal the middle portion, and over the stent, said securement means comprising:
      I) a securement sheath having a proximal end, a distal end, an exterior surface and an interior surface, said securement sheath being slidably mounted on the catheter shaft and being constructed and arranged for proximal retraction along the catheter shaft to expose the stent, the securement sheath having a plurality of flexibility enhancing elements, the plurality of flexibility enhancing elements being dispersed substantially throughout the securement sheath.

7. The apparatus of claim 6, wherein the securement means further comprises, a distal cuff having a proximal end, a distal end, an exterior surface and an interior surface, said distal cuff being mounted near the distal end of the stent and being constructed and arranged to closely surround the exterior surface of the securement sheath at the distal end of the securement sheath until retraction thereof.

8. The apparatus of claim 7 herein the flexibility enhancing elements comprise a plurality of holes in the securement sheath.

9. The apparatus of claim 8 wherein the flexibility enhancing elements comprise a plurality of radial indentations in the securement sheath.

10. The apparatus of claim 7 wherein the flexibility enhancing elements comprise a plurality of dimples in the securement sheath.

* * * * *